US010244989B2

(12) United States Patent
Ottevanger et al.

(10) Patent No.: US 10,244,989 B2
(45) Date of Patent: Apr. 2, 2019

(54) METHOD AND SYSTEM FOR DETECTING CARDIAC TAMPONADE IN A PATIENT

(71) Applicants: Egbert Jan Constant Ottevanger, The Hague (NL); Rienk Rienks, Putten (NL); Wouter Matthijs Muijs Van De Moer, Rotterdam (NL)

(72) Inventors: Egbert Jan Constant Ottevanger, The Hague (NL); Wouter Matthijs Muijs Van De Moer, Rotterdam (NL)

(73) Assignees: Egbert Jan Constant Ottevanger, The Hague (NL); Reink Reinks, Putten (NL); Wouter Matthijs Muijs Van de Moer, Rotterdam (NL)

( * ) Notice: Subject to any disclaimer, the term of this patent is extended or adjusted under 35 U.S.C. 154(b) by 942 days.

(21) Appl. No.: 14/377,896

(22) PCT Filed: Feb. 12, 2013

(86) PCT No.: PCT/NL2013/050082
§ 371 (c)(1),
(2) Date: Aug. 11, 2014

(87) PCT Pub. No.: WO2013/122459
PCT Pub. Date: Aug. 22, 2013

(65) Prior Publication Data
US 2015/0032007 A1 Jan. 29, 2015

(30) Foreign Application Priority Data

Feb. 13, 2012 (NL) ...................................... 2008276

(51) Int. Cl.
*A61B 5/00* (2006.01)
*A61B 8/06* (2006.01)
(Continued)

(52) U.S. Cl.
CPC .......... *A61B 5/7275* (2013.01); *A61B 5/0004* (2013.01); *A61B 5/0205* (2013.01);
(Continued)

(58) Field of Classification Search
CPC .............. A61B 5/7275; A61B 5/02028; A61B 5/02158; A61B 5/6869; A61B 8/065
(Continued)

(56) References Cited

U.S. PATENT DOCUMENTS

2004/0215049 A1* 10/2004 Zdeblick ............ A61B 5/02028
600/16
2004/0220637 A1* 11/2004 Zdeblick ............ A61B 5/02028
607/17
(Continued)

OTHER PUBLICATIONS

Spodick, D. H., "Pathology of Cardiac Tamponade", CHEST, No. 113, May 1998, pp. 1372-1378.*
(Continued)

*Primary Examiner* — Katherine Fernandez
(74) *Attorney, Agent, or Firm* — Thomas|Horstemeyer, LLP (57) ABSTRACT

System for indicating a possibility a cardiac tamponade occurring in a patient, comprising: —a right atrium pressure sensor, configured for measuring a right atrium pressure in a right atrium of the patient; —an intra pericardial pressure sensor, configured for measuring an intra pericardial pressure in a portion of an intra-pericardial space of the patient; —a processing device that is operatively connected to the pressure sensors, is provided with a predetermined statistical distribution of pressure versus tamponade probabilities, and is configured for: —determining a trans-mural pressure difference between the right atrium pressure and the intra pericardial pressure; —comparing the trans-mural pressure difference with the statistical distribution, and —indicating
(Continued)

the possibility of cardiac tamponade occurrence, based on the trans-mural pressure difference comparison.

21 Claims, 3 Drawing Sheets (51) Int. Cl.
*A61B 5/029* (2006.01)
*A61B 5/03* (2006.01)
*A61B 5/053* (2006.01)
*A61B 5/0215* (2006.01)
*A61B 5/02* (2006.01)
*A61B 5/0205* (2006.01)
*A61B 5/027* (2006.01)
*A61B 8/12* (2006.01)

(52) U.S. Cl.
CPC .............. *A61B 5/027* (2013.01); *A61B 5/029* (2013.01); *A61B 5/0215* (2013.01); *A61B 5/02028* (2013.01); *A61B 5/02158* (2013.01); *A61B 5/03* (2013.01); *A61B 5/053* (2013.01); *A61B 5/686* (2013.01); *A61B 5/6869* (2013.01); *A61B 5/7246* (2013.01); *A61B 8/065* (2013.01); *A61B 8/12* (2013.01); *A61B 5/0538* (2013.01)

(58) Field of Classification Search
USPC ......................................................... 600/465
See application file for complete search history.

(56) References Cited

U.S. PATENT DOCUMENTS

2005/0283092 A1   12/2005  Gedebou
2008/0262361 A1*  10/2008  Gutfinger ............. A61B 5/0215
                                                                 600/486
2011/0172545 A1*   7/2011  Grudic .................. A61B 5/021
                                                                 600/485

OTHER PUBLICATIONS

Reddy, P. S., et al., "Cardiac Tamponade: Hemodynamic Observations in Man", Circulation, vol. 58, No. 2, Aug. 1978, pp. 265-272.*
International Search Report Application No. PCT/NL/2013/050082 dated Jul. 29, 2013, 2 pages.
Netherlands Search Report Application No. 2008276 dated Jun. 16, 2012, 2 pages.
Shabetai et al., "The Pericardium and Cardiac Function", Progress in Cardiovascular Diseases, Saunders, Philadelphia, PA, vol. 22, No. 2, Sep. 1, 1979, 25 pp. 107-134.

* cited by examiner

METHOD AND SYSTEM FOR DETECTING CARDIAC TAMPONADE IN A PATIENT

CROSS REFERENCE TO RELATED APPLICATIONS

This application is the National Stage of International Application No. PCT/NL2013/050082, filed 12 Feb. 2013, which claims the benefit of and priority to NL 2008276, filed 13 Feb. 2012, the contents of all of which are incorporated by reference as if fully set forth herein.

TECHNICAL FIELD

The present invention relates to a system and a method for indicating a probability of cardiac tamponade occurring in a patient.

BACKGROUND

After cardiac surgery, it remains a problem as to how to monitor the cardiovascular situation of operated patients. An accumulation of fluid or clot in the intra-pericardial space surrounding the heart may result in a pressure increase in this intra-pericardial space, indicating the occurrence of cardiac tamponade, which constitutes one of the possible complications following cardiac surgery. "Tamponade" means obstruction of blood flow due to a constriction of a blood channel caused by an outside force, in this case the overpressure acting on the heart wall. In this condition, blood is prevented from entering the heart from the veins due to increased pressure in the intra-pericardial space, resulting in a lowering of blood pressure and tachycardia, which if left untreated may result in cardiac death. It is known that cardiac tamponade may occur due to local accumulation of fluid or clot, for example due to bleeding from the pericardial wound bed into the intra-pericardial space, or due to mediastinal bleeding and effusion occurring around the pericardium, any of which being a possible consequence of surgery or trauma. Accumulation of fluid or clot inside a body compartment may be generically indicated as a "compartment syndrome".

Patent document US2005/0283092 discloses a compartment pressure-monitoring device for continuous monitoring of pressure in a localized compartment, with the pericardium presented as an example. The proposed compartment pressure monitoring device comprises a tube (catheter) connected at one end to a pressurizable balloon and a Trocar sleeve for insertion into the compartment, and connected at the other end to a pressure gauge. An alarm device is provided for indicating that the pressure inside the compartment as registered by the inserted tube and balloon exceeds a predetermined pressure, indicating an occurrence of compartment syndrome.

Unfortunately, the device in US2005/0283092 does not enable assessment of cardiac tamponade occurrence probability under various conditions.

SUMMARY

It is an object to provide a system and method that enable improved alerting of the possibility of cardiac tamponade occurring in a patient.

This object is achieved by a system, comprising: —a right atrium pressure sensor, configured for measuring a right atrium pressure in a right atrium of the patient; —an intra pericardial pressure sensor, configured for measuring an intra pericardial pressure in a portion of an intra-pericardial space of the patient; —a processing device that is operatively connected to the pressure sensors, provided with a predetermined statistical distribution of pressure versus tamponade probabilities, and is configured for: —determining a trans-mural pressure difference between the right atrium pressure and the intra pericardial pressure; —comparing the trans-mural pressure difference with the statistical distribution, and —indicating the occurrence probability, based on the trans-mural pressure difference comparison.

The described differential pressure sensor system allows for an improved method of indicating an occurrence probability for cardiac tamponade, for example after cardiac surgery. After a patient has undergone heart surgery, a right atrium access is often maintained in the post-operative period for administering fluids and medications. This access is commonly used to monitor the cardiac preload of the patient, by means of for example right atrium pressure measurements with a pressure sensor. By the addition of an intra pericardial pressure sensor to the pressure measurement system, measurements of fluid pressure within the intra pericardial space may be simultaneously obtained. Elevated pressure in the pericardial space is a unique feature indicating the occurrence of cardiac tamponade. In known methods, as described for example in US2005/0283092, this elevated pressure is directly measured. Instead of directly measuring the intra pericardial pressure, the system proposed herein above enables measurements of a trans-mural pressure difference between the right atrium pressure and the intra pericardial pressure, which provides information on an occurring imbalance between these two regions surrounding the cardiac wall. Due to the differential measurement principle, the proposed system is able to detect cardiac tamponade under both normal and low cardiac preload, which is not possible on the basis of merely pressure readings in the pericardial space alone, i.e. by means of known direct intra pericardial pressure measurement systems. Consequently, also the low pressure tamponade can be detected, which was not possible up to now using known systems. The pressure difference between the right atrium pressure and the intra-pericardial pressure is compared by the processing device to a predefined statistical distribution of pressure versus tamponade probabilities, which may for example be based on results from earlier clinical studies. The probability of cardiac tamponade occurrence resulting from the comparison may be indicated to the user (e.g. the medical specialist), signalling an increased chance of an occurring intra pericardial tamponade. Based on such a possibility indication, the practitioner may decide to investigate further. In one embodiment, the statistical distribution is in its most simplistic form represented by only a predefined trans-mural pressure threshold. Here, a measured drop below the predefined trans-mural pressure threshold may be indicated to the user by a binary indicator. In other embodiments, the statistical distribution and the user indications may contain more detailed information in the form of likelihood graphs.

According to an embodiment, right atrium pressure sensor and the intra pericardial pressure sensor are provided with a joint for fastening the sensors in a button configuration enclosing the inner and outer walls of the right atrium respectively. The right atrium pressure sensor, the intra pericardial pressure sensor, and the joint are then jointly configured for fluid tight enclosure of the right atrium wall, in order to prevent fluid leakage between intra pericardial space and right atrium.

Advantageously, the right atrium pressure sensor and the intra-pericardial pressure sensor can be retained at a mutually fixed configuration, in order to improve the reliability of the trans-mural pressure difference readings. In addition, the joint may be provided with a channel and valve combination configured for exchanging fluids between the right atrium and the intra-pericardial space. The opening and/or closing of the valve may for example be controllable by an actuator in the joint, which is operated based on the trans-mural pressure difference measurements obtained by the two sensors. The intra pericardial pressure sensor may for example be positioned in the pericardial space during an operation (e.g. during open heart surgery, or using a catheter), be subsequently inserted through the right atrium wall into the right atrium, and then connected to an already present atrium pressure sensor, resulting in the sensor button configuration described herein above. Alternatively, a catheter with the right atrium pressure sensor may be configured for puncturing the right atrium wall on the inner right atrium wall using a catheter tip that is provided with a trans-luminal intra-pericardial pressure sensor (TIPPS). Such a catheter tip may comprise a fold-out joint for fastening the TIPPS on the outer right atrium wall inside the intra-pericardial space, resulting in the sensor button configuration described herein above.

According to an embodiment, the system comprises—a reference pressure sensor, configured for measuring a reference pressure at a reference location outside the right atrium and the intra-pericardial space, whereby the processing device is operatively connected to the reference pressure sensor and is configured for: —determining a right atrium pressure difference between the right atrium pressure and the reference pressure, and —indicating the occurrence probability based on differentiating between an ordinary pressure tamponade in case the right atrium pressure difference is above a predetermined right atrium pressure threshold, and a low pressure tamponade in case the right atrium pressure difference is below the right atrium pressure threshold.

The occurrence of low pressure cardiac tamponade is notoriously difficult to register by known direct pressure measurement methods. Usually, low pressure tamponade will only manifest itself after administering additional fluid to the patient. Advantageously, the described system for indicating cardiac tamponade is improved by supplementing the differential cardiac pressure measurements with further pressure measurements in which the direct right atrium pressure is compared with a reference pressure measured outside of the intra pericardial space. The reference pressure sensor may for example be located outside the intra-pericardial space of the patient, and is configured for detecting the reference pressure. The reference pressure sensor may for example be located outside of the patient for determining atmospheric pressure, e.g. a sensor that is an integral part of the processing device, or even positioned at a remote location.

According to a further embodiment, the system comprises—a plurality of intra pericardial pressure sensors, configured for measuring a plurality of intra pericardial pressures at a set of distinct intra-pericardial portions; whereby the pressure processing device is operatively connected to the plurality of intra pericardial pressure sensors, and configured for: —determining a plurality of intra pericardial pressure differences between each of the intra pericardial pressures and the reference pressure; —registering an occurrence of a pressure deviation for any one of the plurality of pressure differences from a set of intra pericardial threshold values, and —correlating the intra-pericardial space with the pressure deviation.

In general, the accumulation of clot, blood, or other fluids may occur locally, or throughout the pericardial space. Advantageously, in an embodiment of the system having multiple intra pericardial pressure sensors at distinct locations inside the pericardial space, cardiac tamponade occurring from local pressure build-up in a compartmentalized intra-pericardial space, for example resulting from local accumulation of fluid or clot, may be registered and localized quickly. The described system enables the study of yet unknown effects of intra-pericardial fluid or clot accumulation on the intra-pericardial pressure distribution, and ultimately on the development of cardiac tamponade. Furthermore, a plurality of pressure sensors assists in preventing a misreading of information due to an isolated measurement error by one of the pressure sensors. By monitoring a plurality of trans-mural pressure differences, with one difference reading for each intra pericardial pressure sensor, it becomes possible to detect compartmentalized tamponade even under low blood filling conditions.

According to another embodiment, the system comprises a cardiac performance detector for measuring an indication of cardiac output for the patient, and whereby the processing device is configured for: —comparing the indication of cardiac output with a stored characteristic value of previous cardiac output measurements, and —adapting the occurrence probability, based on a decrease of the cardiac output larger than a predefined cardiac output drop below the characteristic value.

Measurement of for example the cardiac output provides an indication of the performance of the heart muscle. A decrease of the cardiac output indicates a deterioration of cardiac performance, forming a further indication of the occurrence of cardiac tamponade. According to embodiments, the cardiac output may be intermittently or continuously measured. Due to inter subject differences (between patients) in the normal values for cardiac output, the currently measured cardiac output is preferably compared to a characteristic value of previous cardiac output measurements for the same patient. This characteristic value may be only the latest previous measurement, or a desired statistical average of multiple previous measurements (e.g. obtained by Kalman filtering or similar time averaging techniques). In one embodiment, the occurrence probability used for indicating cardiac tamponade will be altered based on a decrease of the cardiac output that is larger than the allowed (i.e. noise estimate based) decrease, for example by comparison to a predefined output drop value. The cardiac output measurements may be supplemented by measurements of the patient's end tidal partial carbon dioxide pressure level in the respiratory gases (i.e. the carbon dioxide concentration released at the end of expiration). This concentration follows the cardiac output, and can be used as a first indicator for priming detailed cardiac output measurement, and/or as a mutual check.

According to another embodiment, the right atrium pressure sensor is on a distal end of a lead.

This lead may for example be a catheter configured for thermo dilution applications used in cardiac output measurements. The right atrium pressure sensor provided on the distal end of the lead or catheter yields a probe that is reliably insertable and repositionable into the right atrium, and suitable for reading pressures at any desired location in the right atrium. An indication of imminent cardiac tamponade can already be obtained by monitoring the right atrium pressure alone with this lead based right atrium pressure sensor, and by registering a disappearance of the so-called "y descent" deflection in the jugular venous pressure curve resulting from an pericardial pressure impeded filling of the ventricle after tricuspid valve opening.

According to a further embodiment, the lead is an intra cardiac echo catheter, comprising an ultrasound transducer for imaging of and measuring a blood flow in the aorta, and connectable to the processing device, whereby the processing device is configured for: —determining the cardiac output from the measured blood flow and an imaged cross-section of the aorta.

The disadvantage of known thermo dilution methods for measuring cardiac output is that measurement can only be obtained intermittently. Consequently, the acute occurrence of (localized) intra pericardial tamponade may be overlooked in the interval between subsequent dilution based cardiac output measurements. A combination of ultrasound blood flow imaging (e.g. Doppler) and cardiac wall imaging (e.g. time resolved 2- or 3-dimensional echo) yields a relatively accurate method of cardiac performance determination. The cardiac output may for example be derived by relating the imaged aorta diameter (i.e. the perimeter dimensions, for example near the aortic valve) to the time integral of measured blood flow through the aorta (i.e. the temporal flux). Alternatively or in addition, the venous blood inflow into the right atrium (via the superior and/or inferior vena cava) may be imaged by the intra cardiac echo catheter, and deviations in the flow velocities registered. Once the intra-cardiac echo catheter is positioned in the right atrium, the described ultrasound measurements may be executed continuously and at any desired moment. By providing the system with the catheter probe having the both capabilities of continuous pressure reading and ultrasound imaging, a decrease in cardiac output may be noticed with relatively high specificity, and directly related to occurring trans-mural pressure difference deviations. The addition of synchronously measurable cardiac output to the pressure measurements improves the reliability of indicating the occurrence probability of cardiac tamponade. Alternatively, the ultrasound imaging may be conducted intermittently, or be triggered in response to an abrupt change in pressure readings. For example, the imaging measurements may be started at the moment that a decrease in trans-mural pressure difference to below the predetermined trans-mural pressure threshold is detected, or inversely, a pressure drop may initiate ultrasound imaging for providing acknowledgement. Furthermore, the lead may also be configured for both thermo dilution measurements and intra cardiac echo measurements. Advantageously, the cardiac output may then be measured intermittently by either thermo dilution methods or continuously or intermittently by ultrasound measurements.

According to another further embodiment, the cardiac performance detector comprises a thoracic electric bio impedance measurement device that is connectable to the processing device, whereby the processing device is configured for: —determining the cardiac output from a thoracic electric bio impedance measurement between two impedance measurement locations on the patient.

Alternatively or in addition to ultrasound aortic wall and blood flow imaging, the cardiac performance may be (coarsely) monitored by means of thoracic electric bio-impedance (TEB) measurements, using a bio-impedance measurement device. Such a TEB device may for example comprise a plurality of electrodes suitable for attachment to the thorax according to a fixed scheme of electrode positions. The TEB device may for example operate based on determination of both atrial and ventricular filling status as a function of time, by measurement of various potential difference pairs between the plurality of electrodes. The TEB device may be configured for monitoring only a trend in the cardiac output, as absolute measurement values are hard to obtain with contemporary TEB technology. Instead, any deviations in a trend as measured by the TEB device may serve as a trigger for or a mutual check with another cardiac performance assessment method, for instance ultrasound based cardiac performance assessment, in addition to or instead of exploiting the trans-mural pressure readings.

According to another embodiment, the plurality of intra pericardial pressure sensors is arranged in a sensor array and attached to a mesh support that is configured for deployment on and around a portion of an epicardial wall of the patient.

Insertion and proper positioning of the intra pericardial pressure sensor array with mesh support may be executed during cardiac surgery. The inserted array unambiguously defines the positional relationship of the pressure sensors surrounding the epicardium during measurements, for example by means of biomechanical modelling of the heart cycle. Use of the mesh support warrants the spatial integrity of the sensor array, the mesh serving to attach the array to the epicardium and to hold the pressure sensors in their initially planned positions.

According to further embodiments, each intra pericardial pressure sensor comprises a wireless transmission unit for transmitting a wireless signal representing the intra pericardial pressure measurement, and whereby the processing device comprises a receiver unit for receiving the wireless signal.

The use of implantable wireless pressure sensors obviates the need for sensor cabling required for power and signal transmission. Without outward protruding cabling, the outer fibrous pericardium is allowed to heal after surgery, restoring the pericardial pressure balance. Furthermore, by wireless signal transmission, multiple processing devices may simultaneously receive and process the transmitted measurements, and the patient is not motionally impeded by any wiring. According to an embodiment, the pressure sensors are made from bio degradable or absorbable material. Alternatively or in addition, the pressure sensors may be powered by bioelectricity alone.

According to another aspect and in accordance with the effects described herein above, a method is provided for indicating an occurrence probability for cardiac tamponade in a patient, comprising: —measuring a right atrium pressure in a right atrium of the patient; —measuring an intra pericardial pressure in a portion of an intra-pericardial space of the patient; —determining a trans-mural pressure difference between the right atrium pressure and the intra pericardial pressure; —comparing the trans-mural pressure difference with a predetermined statistical distribution of pressure versus tamponade probabilities, and —indicating the occurrence probability, based on the trans-mural pressure difference comparison.

According to an embodiment, the method comprises—measuring a reference pressure at a reference location outside the right atrium and the intra-pericardial space; —determining a right atrium pressure difference between the right atrium pressure and the reference pressure, and —indicating the occurrence probability based on differentiating between an ordinary pressure tamponade in case the right atrium pressure difference is above a predetermined right atrium pressure threshold, and a low pressure tamponade in case the right atrium pressure difference is below the right atrium pressure threshold.

According to an embodiment, the method comprises—comparing the trans-mural pressure difference with a predetermined trans-mural pressure threshold that is approximately 2 mm Hg=267 Pa, and/or whereby the right atrium pressure threshold is approximately 7 mm Hg=933 Pa (see ref.[1]).

A pressure measurement system based on a comparison with threshold values is relatively easy to implement. Practical experience has shown that the given threshold values mark characteristic inflection points of the probability distributions relating the respective pressure readings to the chance of actual occurrence of cardiac tamponade. Consequently, a measurement system based on comparison of trans-mural pressures and/or right atrium pressures to the given threshold values during use will yield an accurate indication of an increased risk of occurring tamponade, with a minimal amount of processing resources. An occurrence of a trans-mural pressure difference below 2 mm Hg will certainly indicate the occurrence of cardiac tamponade.

According to another embodiment, the method comprises—measuring a plurality of intra pericardial pressures at a set of distinct intra-pericardial portions; —determining a plurality of intra pericardial pressure differences between each of the intra pericardial pressures and the reference pressure; —registering an occurrence of a pressure deviation for any one of the plurality of pressure differences from a set of intra pericardial threshold values, and —correlating the intra-pericardial portion with the pressure deviation.

According to yet another embodiment, the method comprises—measuring an indication of cardiac output for the patient; —comparing the indication of cardiac output with a characteristic value of previous cardiac output measurements, and —adapting the occurrence probability, based on a decrease of the cardiac output larger than a predefined cardiac output drop below the characteristic value.

According to a further embodiment, the method comprises—ultrasound imaging of a cross-section of the aorta through a right atrium wall; —measuring a blood flow in the aorta, and —determining the cardiac output from the blood flow and the cross-section.

Preferably, the ultrasound transducer is positioned in the right atrium with its imaging aperture located at or near the right atrium wall and directed toward the ascending aorta near a curved portion. By positioning the transducer with its ultrasound imaging beam (i.e. the ultrasonic main axis) near a curved ascending aorta portion, the ultrasound imaging beam can be directed substantially along the aortic blood flow located up/downstream beyond the curved portion, which enables more accurate Doppler flow-measurements along the ascending aorta. Thus, the accuracy of the continuous ultrasound based method of cardiac output measurement is improved.

According to another further embodiment, the method comprises—measuring a thoracic electric bio impedance between two impedance measurement locations on the patient; —determining the cardiac output from the thoracic electric bio impedance measurement.

BRIEF DESCRIPTION OF THE DRAWINGS

Embodiments will now be described, by way of example only, with reference to the accompanying schematic drawings in which corresponding reference symbols indicate corresponding parts, and in which.

The figures are only meant for illustrative purposes, and do not serve as restriction of the scope or the protection as laid down by the claims.

DETAILED DESCRIPTION

Figure 1:
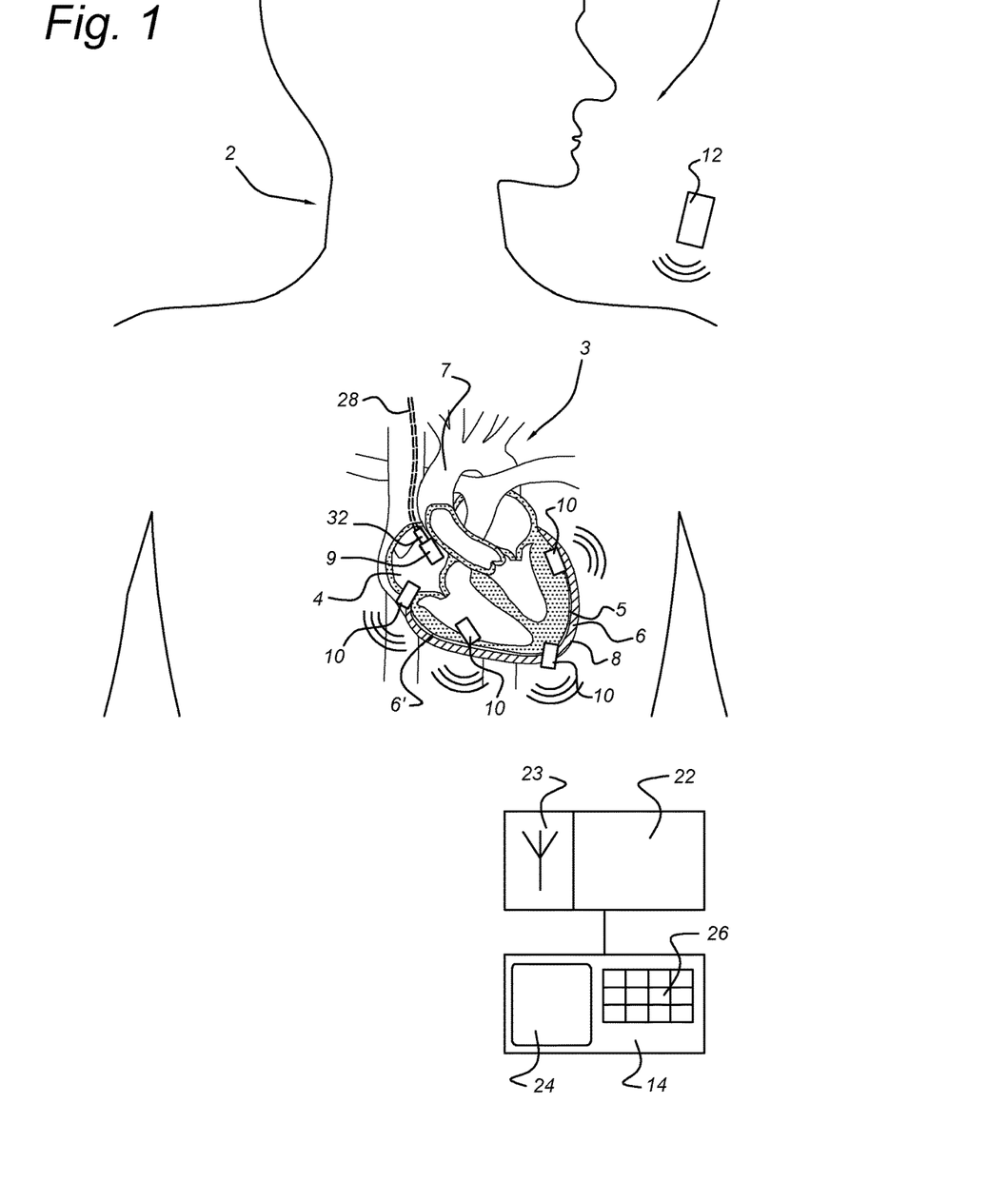
FIG. 1 schematically shows an embodiment of a system for indicating an occurrence probability for cardiac tamponade in a patient.

FIG. 1 shows a system 1 for indicating a probability of cardiac tamponade occurring in a patient 2. The pericardium 8 (also called the pericardial sac) is a sac-like membrane that contains the heart 3. The pericardium 8 consists of an outer fibrous layer and an inner serous layer. The fibrous pericardium constitutes a tough outer sac, and the inner serous layer is thin and located adjacent to the outer surface of the heart muscle (i.e. the epicardium 5, sometimes called the visceral pericardium). Excessive fluid or clot accumulation in the intra-pericardial space 6 (i.e. the space between the outer pericardial fibrous layer and the external surface of the heart) may cause substantial increases in intra-pericardial pressure, with hemodynamic consequences of decreased cardiac performance and hypotension (a condition known clinically as cardiac tamponade. The cardiac tamponade indication system 1 shown in FIG. 1 comprises a multitude of pressure sensors 10 that are configured for measuring a plurality of intra pericardial space pressures Pip at a set of measurement locations within the intra-pericardial space 6 around the heart 3 of a patient 2. The system 1 also has a further pressure sensor 9 for measuring a right atrium pressure Pra in a right atrium 4 of the patient 2, this right atrium pressure sensor 9 being provided on the distal end of a lead 28. Furthermore, the measurement system 1 has a reference pressure sensor 12 that is positioned at a reference location outside the right atrium 4 and outside the intra-pericardial space 6, the reference pressure sensor 12 being configured for measuring a reference pressure Pref.

The measurement system 1 comprises a processing device 14 that is operatively connected or coupled to the right atrium pressure sensor 9, to the plurality of intra pericardial pressure sensors 10, and to the reference pressure sensor 12, for receiving pressure data from the respective pressure sensors 9, 10, 12. Each intra pericardial pressure sensor 10 is surgically implantable and provided with a wireless communication unit for wireless transmission of any pressure reading Pip to the processing device 14. Similarly, the processing device 14 has a wireless receiving unit 22 with an antenna 23 for receiving the wireless transmission of any pressure measurement Pip from any of the implantable pressure sensors 10 or the reference pressure sensor 12. Two-way communication means between the processing device 14 and the pressure sensors 9, 10, 12 may also be provided, so as to allow a user (e.g. medical practitioner) to request pressure readings from selected pressure sensors 9, 10, 12, as well as to activate/deactivate any pressure sensor 9, 10, 12 at will.

The processing device 14 provides for direct user input/output capabilities by means of a visual display 24 (which may be supplemented by other interface means 26 e.g. keyboard, voice command, a control panel, etc). Optionally, the processing device 14 may further be arranged to communicate with an external control device (e.g. a computer arrangement or other interfacing unit; not shown) that provides control and/or data access to the user. The processing device 14 may also receive data from various other components, as discussed below with reference to FIG. 2.

The processing device 14 shown in FIG. 1 is provided with a predetermined statistical distribution of pressure versus tamponade probabilities. Furthermore, the processing device 14 is configured for determining a trans-mural pressure difference ΔPtm between the right atrium pressure Pra and the intra pericardial pressure Pip, and configured for comparing the trans-mural pressure difference with the statistical distribution. The processing device 14 is then configured for indicating the occurrence probability, based on the trans-mural pressure difference comparison. Also, the processing device 14 is configured for determining a right atrium pressure difference ΔPra between the right atrium pressure Pra and the reference pressure Pref, and for refining the indication of occurrence probability, the refinement being based on differentiating between an ordinary pressure tamponade in case the right atrium pressure difference ΔPra is above a predetermined right atrium pressure threshold TPra, and a low pressure tamponade in case the right atrium pressure difference ΔPra is below the right atrium pressure threshold TPra.

Furthermore, the processing device 14 shown in FIG. 1 is configured for determining a plurality of pressure differences ΔPip between each of the plurality of measured pressures Pip and the obtained reference pressure Pref. The processing device 14 is further configured for detecting an occurrence of a pressure deviation for any of the plurality of pressure differences ΔPip from a preset pericardial pressure threshold TPip. Furthermore, the processing device 14 is configured for correlating the pressure measurement location to the intra-pericardial space portion 6', so as to equate the location of pressure deviation with the localized intra-pericardial tamponade.

The method of localizing a cardiac tamponade induced by at least an intra-pericardial portion 6' of the intra-pericardial space 6 of a patient 2 comprises the positioning of a plurality of pressure sensors 10 at a set of measurement locations within the intra-pericardial space 6, e.g. by surgical implantation, and obtaining measurements of a plurality of intra-pericardial pressures Pip. As is further explained with reference to FIG. 3, embodiments of the method further comprise positioning at least one reference pressure sensor 12 at a reference location outside the pericardial space 6, and obtaining a reference pressure Pref at the reference location. Subsequently, a plurality of pressure differences ΔPip between each of the pressures Pip and the reference pressure Pref is determined. The plurality of pressure differences is then evaluated and any deviation occurring for each of the plurality of the individual pressure differences ΔPip from a predetermined pressure threshold Tpip is registered. A registered pressure deviation is exploited by correlating the measurement location in which the pressure deviation occurs, to the intra-pericardial space portion 6' that is assumed to be involved in or responsible for inducing the cardiac tamponade.

Figure 2:
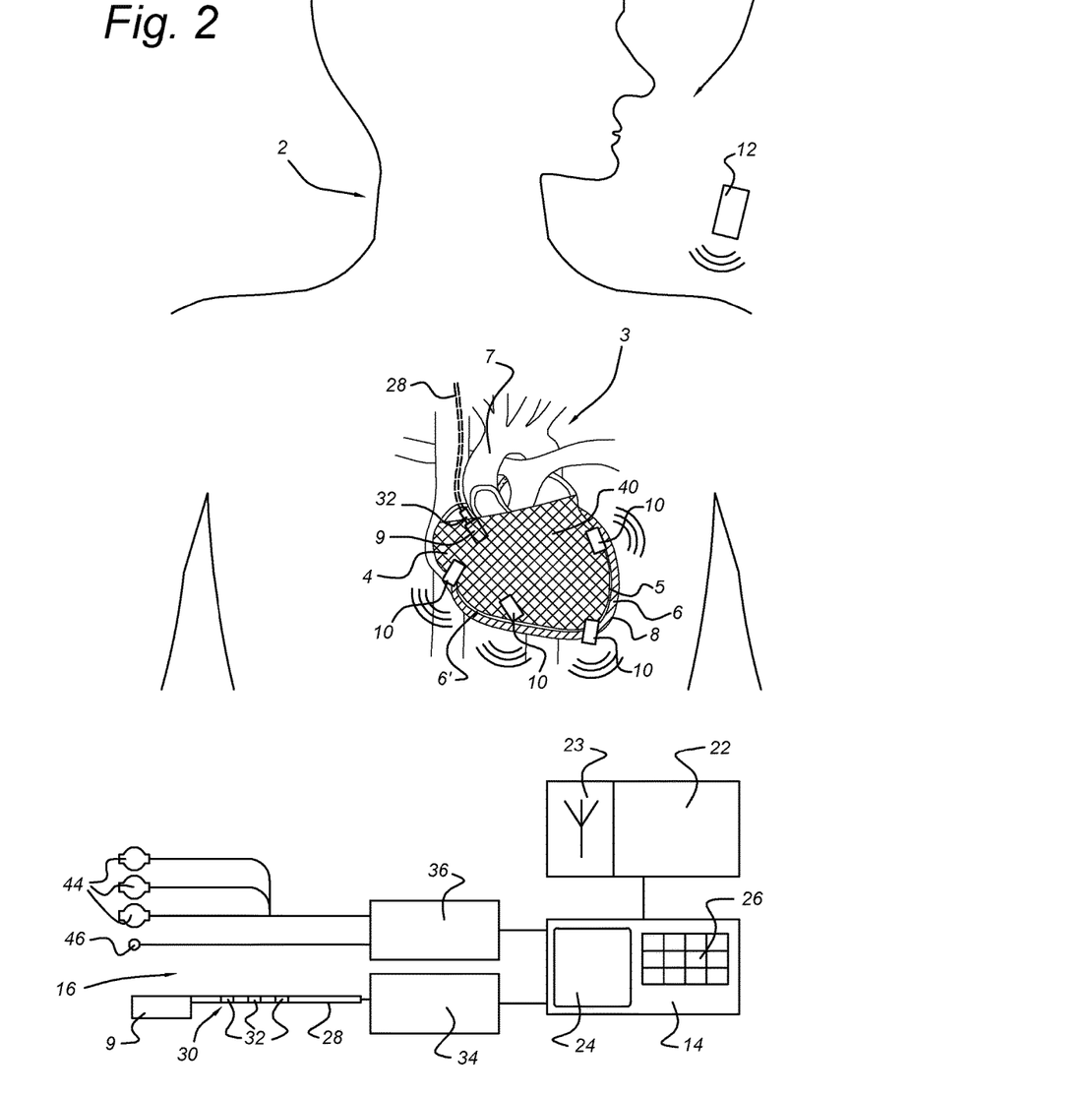
FIG. 2 schematically shows an embodiment of a system for indicating and localizing an occurrence probability for cardiac tamponade in a patient, the system comprising an ultrasound imaging device.

In the embodiment of the tamponade measurement system 1 shown in FIG. 2, the system 1 has cardiac performance detection means 16 for measuring indications of cardiac output Φco for the patient 2. Here, the processing device 14 is configured for: comparing the indication of cardiac output Φco with a stored characteristic value Φprev of previous cardiac output measurements, and adapting the occurrence probability, based on a decrease of the cardiac output Φco larger than a predefined cardiac output drop Dco below the characteristic value Φprev.

The system 1 comprises a thoracic electric bio impedance measurement device 36 with a plurality of electrodes 44 fixable to predetermined measurement locations on the patient's thorax. The electrodes 44 are configured for collecting thoracic electric bio impedance readings Zteb between two impedance measurement locations, and monitoring the heart cycle based on these impedance measurements. The thoracic electric bio impedance measurement device 36 is connectable to the processing device 14 for transmitting the collected impedance measurements. It is a known technique that the electrical impedance or potential difference between two electrodes 44 may be intermittently or continuously measured (see for example ref [2]). With the bio-impedance measurement technique, the cardiac performance of the heart 3 may be (approximately) measured.

The measurement system 1 of FIG. 2 comprises a lead 28 formed as an intra cardiac echo catheter 30 carrying both the right atrium pressure sensor 9 and a phased array ultrasonic imaging device or transducer 32 (e.g. circular ultrasonic transducer elements in a ring-shape around the catheter), and configured for measuring a blood flow velocity in the aorta 7 via Doppler imaging. The ultrasound transducer 32 is communicatively coupled to an ultrasound processing device 34, which in turn is coupled to the processing device 14, so as to enable the latter to determine the cardiac output Φco from the measured blood flow and an imaged cross-section of the aorta 7.

FIG. 2 also depicts a net, mesh support, or heart basket 40 that is deployable on the epicardium 5, and which includes the plurality of pressure sensors 10, arranged in a sensor array configuration and fixed to the deployable net 40. The net 40 serves as a deployable platform around and covering a portion of the epicarcium 5, for attaching and keeping the pericardial pressure sensors 10 in a fixed position with respect to the epicardium 5.

The indication and/or localization system 1 according to the present invention may take a variety of specific forms, including both especially designed and commercial-off-the-shelf components. Conventional and commercially available pressure sensors 9, 10, 12 and/or electrodes 44 may be employed, but also sensors that are particularly tailored and optimized to perform the task as described here. In general, known computer arrangements (workstations, personal computers, etc.) may be programmed to perform any or all of the functions and calculations of the system and method as described herein.

Figure 3:
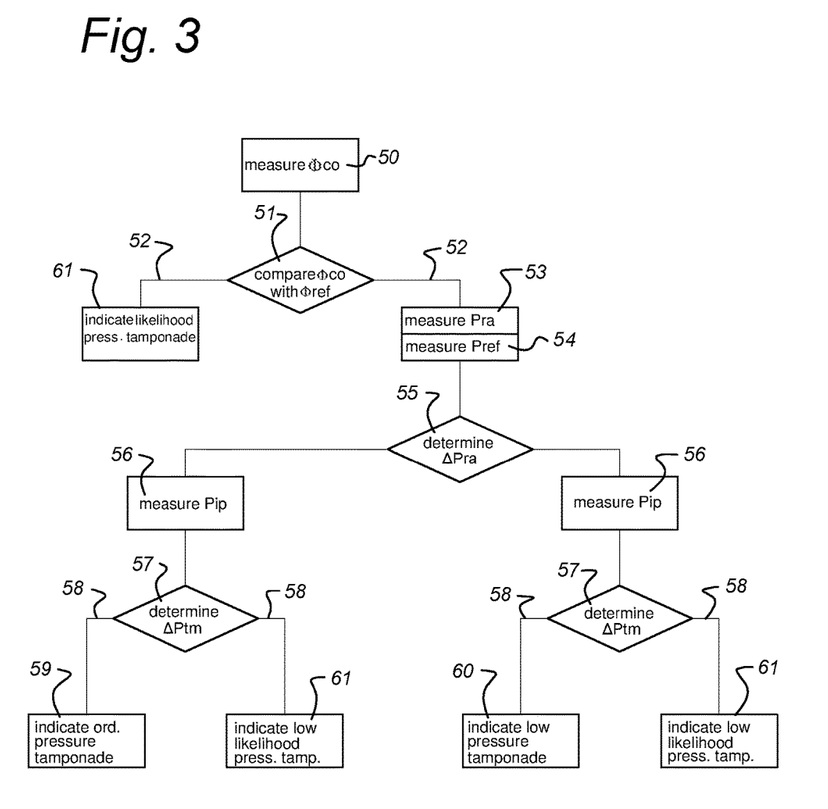
FIG. 3 presents a flow chart for a method of indicating a probability of cardiac tamponade occurrence.

FIG. 3 illustrates a detailed embodiment of a method of indicating an occurrence probability for cardiac tamponade in a patient 2. This method comprises the following actions:

Measuring 50 an indication of cardiac output Φco for the patient 2. This action 50 may for example be achieved by ultrasound imaging of a cross-section of the aorta 7 through a right atrium 4 wall, by measuring a blood flow in the aorta 7, and by determining the cardiac output Φco from the blood flow and the cross-section. Alternatively or in addition, this action 50 may be achieved by measuring a thoracic electric bio impedance between two impedance measurement locations 37 on the patient 2, and determining the cardiac output Φco from the thoracic electric bio impedance measurement.

Comparing 51 the indication of cardiac output Φco with a characteristic value Φprev of previous cardiac output measurements.

Adapting 52 the occurrence probability for cardiac tamponade, based on a decrease of the cardiac output Φco larger than a predefined cardiac output drop below the characteristic value Φprev.

Subsequently, measuring 53 a right atrium pressure Pra in a right atrium 4 of the patient 2.

Simultaneously, measuring 54 a reference pressure Pref at a reference location outside the right atrium 4 and outside the intra-pericardial space 6;

Determining 55 a right atrium pressure difference ΔPra between the right atrium pressure Pra and the reference pressure Pref. In this action 55, the right atrium pressure difference ΔPra may for example be compared to a right atrium pressure threshold TPra of approximately 7 mm Hg=933 Pa.

In order to differentiate between an ordinary tamponade and a low pressure tamponade, measuring 56 an intra pericardial pressure Pip in an intra-pericardial space portion 6' of the patient 2.

Determining 57 a trans-mural pressure difference ΔPtm between the right atrium pressure Pra and the intra pericardial pressure Pip.

Comparing 58 the trans-mural pressure difference ΔPtm with a predetermined statistical distribution of pressure versus tamponade probabilities. In this action 58, the trans-mural pressure difference ΔPtm may for example be compared 58 with a predetermined trans-mural pressure threshold TPtm that is approximately 2 mm Hg=267 Pa.

Indicating 59, 60 the occurrence probability, based on the comparison 58 of the trans-mural pressure difference ΔPtm. In this action 59, 60, the occurrence probability may be related to differentiating between an ordinary pressure tamponade 59 in case the right atrium pressure difference ΔPra is above a predetermined right atrium pressure threshold TPra of approximately 7 mm Hg=933 Pa, and a low pressure tamponade 60 in case the right atrium pressure difference ΔPra is below the right atrium pressure threshold TPra. A low likelihood of pressure tamponade occurrence may be indicated 61 if ΔPtm, after comparison 58 with the predetermined trans-mural pressure threshold TPtm, exceeds this trans-mural pressure threshold value of 2 mm Hg=267 Pa.

Furthermore, in the action of measuring 56 an intra pericardial pressure Pip in an intra-pericardial space portion 6' of the patient 2, a plurality of intra pericardial pressures Pip at a set of distinct intra-pericardial portions 6' may be measured instead (not shown), followed by determining a plurality of intra pericardial pressure differences ΔPip between each of the intra pericardial pressures Pip and the reference pressure Pref.

Subsequently, an occurrence of a pressure deviation Dp for any one of the plurality of pressure differences ΔPip from a set of intra pericardial threshold values TPip is registered, and the pressure deviation Dp is correlated with the intra-pericardial portion 6' in which the pressure deviation occurs.

The descriptions above are intended to be illustrative, not limiting. It will be apparent to the person skilled in the art that alternative and equivalent embodiments of the invention can be conceived and reduced to practice, without departing from the scope of the claims set out below.

REFERENCES

[1] Sagristà-Sauleda et al, "Low Pressure Cardiac Tamponade: Clinical and Hemodynamic Profile", Circulation 2006, 114(9), pp. 945-952

[2] Konings et al, "In-vivo validation of a new non-invasive continuous ventricular stroke volume monitoring system in an animal model", Critical Care 2011, 15:R165

LIST OF FIGURE ELEMENTS 1 tamponade measurement system
2 patient
3 heart
4 right atrium
5 epicardium
6 intra-pericardial space
6' intra-pericardial portion
7 aorta
8 pericardium
9 right atrium pressure sensor
10 intra-pericardial pressure sensor
12 reference pressure sensor
14 processing device
16 cardiac performance detector
22 receiver unit
23 antenna
24 visual display unit
26 input/output
28 lead
30 intra cardiac echo catheter
32 ultrasound transducer
34 ultrasound processing device
36 thoracic electric bio impedance measurement device
37 impedance measurement location
38 sensor array
40 mesh support
44 electrode
46 reference electrode
50 measure indication of cardiac output Φco
51 compare indication of cardiac output Φco with characteristic value Φprev
52 adapt occurrence probability for cardiac tamponade
53 measure right atrium pressure Pra
54 measure reference pressure Pref
55 determine right atrium pressure difference ΔPra
56 measure intra-pericardial pressure Pip
57 determine trans-mural pressure difference ΔPtm
58 compare trans-mural pressure difference with statistical distribution of pressure versus tamponade probabilities
59 indicate ordinary pressure tamponade occurrence
60 indicate low pressure tamponade occurrence
61 indicate low likelihood of pressure tamponade
Pra right atrium pressure
Pip intra pericardial space portion pressure
Pref reference pressure
ΔPra right atrium pressure difference
ΔPtm trans-mural pressure difference
TPtm trans-mural pressure threshold
TPra right atrium pressure threshold
TPip pericardial pressure threshold
Φco cardiac output
Φprev characteristic cardiac output
Dco allowed cardiac output drop
Dp pressure deviation
Zteb thoracic electric bio impedance

The invention claimed is:

1. A system for indicating an occurrence probability for cardiac tamponade in a patient, the system comprising:
a right atrium pressure sensor, configured for measuring a right atrium pressure in a right atrium of the patient;
an intra-pericardial pressure sensor, configured for measuring an intra-pericardial pressure in a portion of an intra-pericardial space of the patient;
a reference pressure sensor, configured for measuring a reference pressure at a reference location outside the right atrium and the intra-pericardial space,
a processing device that is operatively connected to the pressure sensors, and that is provided with a predetermined statistical distribution of predetermined transmural pressure differences versus occurrence probabilities for cardiac tamponade, wherein the predetermined transmural pressure differences are predetermined differences between the right atrium pressure and the intra-pericardial pressure; and an output device configured for outputting an occurrence probability for cardiac tamponade in the patient to a user from the processing device, wherein the processing device is configured for:

determining a measured trans-mural pressure difference between a right atrium pressure measured by the right atrium pressure sensor and an intra-pericardial pressure measured by the intra-pericardial pressure sensor, determining a measured right atrium pressure difference between the right atrium pressure measured by the right atrium pressure sensor and the reference pressure measured by the reference pressure sensor, comparing the measured transmural pressure difference with the predetermined statistical distribution, determining the occurrence probability for cardiac tamponade, based on said comparing the measured transmural pressure difference with the predetermined statistical distribution, and refined by differentiating between a first type of tamponade if the measured right atrium pressure difference is above a predetermined right atrium pressure threshold, and a second type of tamponade if the measured right atrium pressure difference is below the right atrium pressure threshold, and indicating the determined occurrence probability for cardiac tamponade to a user by the output device.

2. The system according to claim 1, further comprising:
a plurality of intra-pericardial pressure sensors, configured for measuring a plurality of intra-pericardial pressures at a set of distinct intra-pericardial portions;
wherein the processing device is operatively connected to the plurality of intra-pericardial pressure sensors, and wherein the processing device is further configured for:
determining a plurality of measured intra-pericardial pressure differences between each of the intra-pericardial pressures and the reference pressure;
registering an occurrence of a pressure deviation for any one of the plurality of measured pressure differences from an intra-pericardial pressure threshold, and
correlating the pressure deviation with the intra-pericardial space portion location.

3. The system according to claim 2, wherein the plurality of intra-pericardial pressure sensors is arranged in a sensor array and attached to a mesh support that is configured for deployment on and around a portion of an epicardium of the patient.

4. The system according to claim 2, wherein each intra-pericardial pressure sensor comprises a wireless transmission unit for transmitting a wireless signal representing the intra pericardial pressure measurement, and wherein the processing device further comprises a receiver unit for receiving the wireless signal.

5. The system according to claim 1, further comprising a cardiac performance detector for measuring cardiac output for the patient, and wherein the processing device is further configured for:
comparing the measured cardiac output with a stored characteristic value of previous cardiac output measurements, and adapting the occurrence probability for cardiac tamponade, based on a decrease of the measured cardiac output larger than a predefined cardiac output drop below the characteristic value.

6. The system according to claim 5, wherein the cardiac performance detector further comprises a thoracic electric bioimpedance measurement device that is connectable to the processing device, wherein the processing device is further configured for:
determining the cardiac output from a thoracic electric bioimpedance measurement between two impedance measurement locations on the patient.

7. The system according to claim 1, wherein the right atrium pressure sensor is on a distal end of a lead.

8. The system according to claim 7, wherein the lead is an intra-cardiac echo catheter, comprising an ultrasound transducer for imaging of and measuring a blood flow in the aorta, and connectable to the processing device, wherein the processing device is further configured for:
determining cardiac output from the measured blood flow and an imaged cross-section of the aorta.

9. The system according to claim 1, wherein the right atrium pressure sensor and the intra-pericardial pressure sensor are provided with a joint configured to enclose the inner and outer walls of the right atrium, wherein the joint is provided with a channel and valve combination configured for exchanging fluids between the right atrium and the intra-pericardial space.

10. The system according to claim 1, wherein the statistical distribution is represented by a predefined transmural pressure threshold, and wherein the output device outputs a binary indicator from the processing device.

11. The system according to claim 1, wherein the output device provides a likelihood graph.

12. The system according to claim 1, wherein the output device comprises a visual display.

13. The system according to claim 1, wherein the right atrium pressure threshold is approximately 7 mm Hg=933 Pa.

14. A method of indicating an occurrence probability for cardiac tamponade in a patient, the method comprising:
determining a measured transmural pressure difference between a right atrium pressure measured in a right atrium of the patient, and an intra-pericardial pressure measured in a portion of an intra-pericardial space of the patient,
determining a measured right atrium pressure difference between the measured right atrium pressure and a reference pressure measured at a reference location outside the right atrium and the intra-pericardial space,
comparing the measured transmural pressure difference with a predetermined statistical distribution of predetermined transmural pressure differences versus occurrence probabilities for cardiac tamponade, wherein the predetermined transmural pressure differences are predetermined differences between the right atrium pressure and the intra-pericardial pressure,
determining the occurrence probability for cardiac tamponade, based on said comparing the measured transmural pressure difference with a predetermined statistical distribution, and refined by differentiating between a first type of tamponade if the measured right atrium pressure difference is above a predetermined right atrium pressure threshold, and a second type of tamponade if the measured right atrium pressure difference is below the right atrium pressure threshold, and indicating the determined occurrence probability for cardiac tamponade on an output device configured for outputting the determined occurrence probability for cardiac tamponade to a user.

15. The method according to claim 14, further comprising:

comparing the measured transmural pressure difference with a predetermined transmural pressure threshold that is approximately 2 mm Hg=267 Pa.

16. The method according to claim 14, further comprising:

determining a plurality of measured intra-pericardial pressure differences between each of a plurality of intra-pericardial pressures measured at a set of distinct intra-pericardial portions, and the reference pressure;

registering an occurrence of a pressure deviation for any one of the plurality of measured pressure differences from a set of intra-pericardial threshold values, and correlating the intra-pericardial portion with the pressure deviation.

17. The method according to claim 14, further comprising:

comparing a measured cardiac output for the patient with a characteristic value of previous cardiac output measurements, and adapting the occurrence probability for cardiac tamponade, based on a decrease of the measured cardiac output larger than a predefined cardiac output drop below the characteristic value.

18. The method according to claim 17, further comprising:

ultrasound imaging of a cross-section of the aorta through a right atrium wall, and determining the cardiac output from a blood flow measured in the aorta and the cross-section.

19. The method according to claim 17, further comprising:

determining the cardiac output from a thoracic electric bioimpedance measurement between two impedance measurement locations on the patient.

20. The method according to claim 14, wherein the output device is a visual display.

21. The method according to claim 14, wherein the right atrium pressure threshold is approximately 7 mm Hg=933 Pa.

* * * * *